United States Patent [19]

Huling

[11] 4,331,629

[45] * May 25, 1982

[54] STEAM AND WATER CONSERVATION SYSTEM FOR PASTEURIZERS

[75] Inventor: James K. Huling, Belleville, Ill.

[73] Assignee: Barry-Wehmiller Company, St. Louis, Mo.

[*] Notice: The portion of the term of this patent subsequent to Apr. 21, 1998, has been disclaimed.

[21] Appl. No.: 187,568

[22] Filed: Sep. 15, 1980

[51] Int. Cl.³ .......................... A61L 2/04; A61L 2/24; A23C 3/027; A23L 3/04

[52] U.S. Cl. .......................... 422/25; 99/361; 99/362; 422/105; 422/114; 422/302; 422/304; 426/397

[58] Field of Search .......... 422/25, 105, 114, 115, 422/302, 304; 426/397; 99/361, 362, 363

[56] References Cited

U.S. PATENT DOCUMENTS

| | | | |
|---|---|---|---|
| 2,282,187 | 5/1942 | Herold et al. | 99/362 X |
| 2,333,544 | 11/1943 | Meyer | 99/361 |
| 2,466,769 | 4/1949 | Herold et al. | 99/362 X |
| 2,658,608 | 11/1953 | Wehmiller | 198/776 |
| 3,622,357 | 11/1971 | Tillman | 99/362 X |
| 4,263,254 | 4/1981 | Huling | 422/25 |
| 4,279,858 | 7/1981 | Huling | 422/25 |

FOREIGN PATENT DOCUMENTS

2369866 7/1978 France ................................. 99/483

Primary Examiner—Barry S. Richman
Attorney, Agent, or Firm—Gravely, Lieder & Woodruff

[57] ABSTRACT

In the pasteurizing of beverages and comestibles in closed containers, the containers are progressively raised in temperature to the pasteurizing temperature and, after an appropriate period of time, progressively cooled down in apparatus which practices a method for separately storing both heated water and cooled water and applying the heated and cooled water from storage so that skips in the supply of containers will be accommodated with savings in the amount of steam and chilled water required.

5 Claims, 6 Drawing Figures

STEAM AND WATER CONSERVATION SYSTEM FOR PASTEURIZERS

BACKGROUND OF THE INVENTION

1. Field of the Invention

This invention is directed to an improved system of conserving steam and water in pasteurizers, as well as providing apparatus for reducing the cost of effecting pasteurization of beverages.

2. Description of the Prior Art

The need for pasteurizing beverages has been known for many years, principally for control of harmful germs in beverages, and to preserve product flavor and extend shelf life. The use of water sprays or showering means in pasteurizing apparatus of common ownership with the present application has been disclosed in the early patents of Herold et al U.S. Pat. Nos. 2,282,187, issued May 5, 1942, and 2,466,769 issued Apr. 12, 1949. Other types of pasteurizers are disclosed in Meyer 2,333,544 issued Nov. 21, 1943 and Tillman 3,622,357 issued Nov. 23, 1971.

A pasteurizer having a system for conserving energy by providing a source of heated water to reduce the use of steam has been disclosed by Huling in application Ser. No. 062,693, filed Aug. 1, 1979, now U.S. Pat. No. 4,263,254 issued Apr. 21, 1981. A further pasteurizer improvement for conserving energy by providing an auxiliary source of chilled water has been disclosed by Huling in application Ser. No. 097,511, filed Nov. 20, 1979, now U.S. Pat. No. 4,279,858 issued July 21, 1981. In these applications, the principal aim is limited for accomplishing a particular purpose.

The problems with these earlier forms of pasteurizers reside in the great size of apparatus, the cost of the energy to transfer heat and cooling to thousands of beverage containers, and the tremendous quantities of water and steam needed to carry out the necessary basic steps of heating, holding at pasteurizing temperature levels, and cooling. The cost of the energy used up on a single container is insignificant, but when it is figured up in terms of a pasteurizing process for handling large numbers of containers per hour, the energy cost becomes significantly high. For example, a pasteurizer rated to process 72,000 bottles of beer per hour can use steam at a cost as high as $25.00 per hour or $100,000 per 4000 hour year, and the water cost can be of the order of $21.00 per hour or $84,000 per year. These figures are applicable without regeneration.

Cost can be reduced if regeneration is incorporated as taught by Huling in the foregoing disclosures. In the normal case of beer entering the pasteurizer at a temperature level of about 34° F, the containers absorb heat from water, cooling the water and raising the beer temperature toward pasteurizing levels. The cooled water is sprayed over the containers in the cooling zone after pasteurization to absorb the heat and cool the beer before discharge to the outside. A thermal balance is achieved, and the beer containers are discharged at a temperature level of the order of 80° F. A perfectly balanced theoretical example could eliminate the water cost and cut the steam cost to about $13.60. The result would be reducing costs from about $184,000 to about $54,000 for a sayings of the order of $130,000 per year. A pasteurizer operating at about 85% efficiency is a more practical case to consider, but as that level there are "gaps" in the supply of containers which upset the thermal balance. When the gaps (or skippers) show up in the load end of the pasteurizer, cold water has to be used for lack of the cold beer. When gaps or skippers are present in the discharge end steam, has to be used to substitute for the lack of hot beer. Under conditions of this example, cost would rise and the quantity of containers would drop.

SUMMARY OF THE INVENTION

The present form of pasteurizer is proposed to overcome the problems discussed above, such as high cost, and excessive use of steam and water. Cost savings are obtainable based on four pairs of regenerative zones in a pasteurizer. When a gap (or skipper) is present in the load end of the pasteurizer where normal pre-heating takes place, water is introduced to maintain the thermal balance. Normally, this water would be discharged from the pasteurizer at a relatively high temperature.

The steam conservation feature of the present system stores this latter high temperature water until the gap moves out of the pre-heating zones and moves into the pre-cooling end of the pasteurizer, and at that time, the stored water is injected into these pre-cooling zones in place of steam. This provision for steam conservation allows water to be stored at relatively high temperature, thereby reducing need for steam. It reflects a savings of approximately seventy-five (75%) percent of the steam required in these zones.

The water conservation feature of this invention makes use of the low temperature water that is discharged from the steam conservation. This water is relatively cold and when a gap appears in the load end of the pasteurizer, the water is used instead of outside local water or refrigerated water. This effects a savings of approximately one-half the water that has heretofore been used in the regeneration zones.

With the use of the steam and water conservation features in the four zone regeneration type pasteurizers, to be more fully described, it is possible to approach more closely an ideal operation. Even so, some breweries desire the beer to be lower in temperature than what can be achieved through the regeneration methods of this disclosure, and additional outside cooling water is required. However, the added cool water can be made use of or be complementary to the discharge water from the steam conservation method, such cool water being acquired from the water conservation method.

While the foregoing applies to the present improvements, there are temporary thermal unbalance conditions when considerable steam and outside water is required regardless of regeneration. One condition is when production first starts up and steam must be supplied, and another condition is at the end of a production run during container runout when a substantial amount of water is required to continue to pre-cool the containers to the desired discharge temperature.

The principal objects of the present invention are to provide a pasteurizer with a system of combined steam and water conservation such that economies can be achieved, and to substantially maintain thermal balance in the load end and in the runout end when skippers occur.

Other objects of the invention are to obtain cost savings by conserving the water in the system in both high and low temperature phases, thereby reducing amounts of outside steam and water required in normal or average pasteurizing cycles, and to obtain overall cost savings without unduly sacrificing efficiency in pasteurizing containers.

Still further objects will be set forth in the following description of a preferred embodiment.

BRIEF DESCRIPTION OF THE DRAWINGS

The present invention is illustrated in the accompanying drawings, wherein.

DETAILED DESCRIPTION OF THE EMBODIMENTS

The structure of the pasteurizer seen in the accompanying drawings comprises a conveyor 9 for moving containers through sprays associated with a series of temperature zones in the pasteurizing tunnel from the load end at tank 10. The preheating zones are defined by the location of a series of water tanks 10, 11, 12 and 13 associated with first, second, third and fourth zones of container preheating. Water showering means 16 are over tank 10; showering means 17 over tank 11; showering means 18 over tank 12; and showering means 19 over tank 13.

Following the fourth preheating zone, there is a fifth zone including a hot water storage tank 20, and following that tank is a tank 21 which catches water from showering means 22 which is delivered at the desired pasteurizing temperature. Since the pasteurizing temperature must be held for the required time, there is a sixth zone associated with a tank 23 for collecting water from showering means 24. Following the sixth zone, there are pre-cooling zones in series defined by a first pre-cooling tank 25 in zone seven; a second pre-cooling tank 26 in zone eight; a third pre-cooling tank 27 in zone nine; and a fourth pre-cooling tank 28 in zone ten. These tanks are associated beneath respective water showering means 29, 30, 31 and 32. A water collecting tank 33 in zones ten and eleven follows the fourth pre-cooling tank 28, and a final cooling water collecting tank 34 is disposed at the discharge end of the pasteurizer in association with showering means 35.

The water collecting tanks 10 and 11 in the load end are separated by a wall forming an overflow weir 36, and similar weirs 37 and 38 are disposed between tanks 11 and 12, and between tanks 12 and 13, respectively. These weirs 36, 37 and 38 are provided to allow the water to flow in series from tank 10 to tank 11, and from tank 11 to tank 12, and from tank 12 to tank 13. In the discharge end of the pasteurizer, tanks 25 and 26 are separated by a weir 39, and similar weirs 40 and 41 separate tanks 26, 27 and 27, 28. Thus, the water is enabled to overflow from tank 25 through tanks 26, 27 and 28.

Tank 20 (FIG. 1A) has a special function to collect heated water under the cover 20A so that water from showering means 19 and 22 will be directed into tank 13, and into tank 20 which collects the water at slightly less than pasteurizing temperature. The collecting tank 33 (FIG. 1B) has a special function and is provided with a cover 33A so that water from showering means 32 can drain off to tank 28, and water from showering means 35 can drain off into tank 34.

Figure 1A:
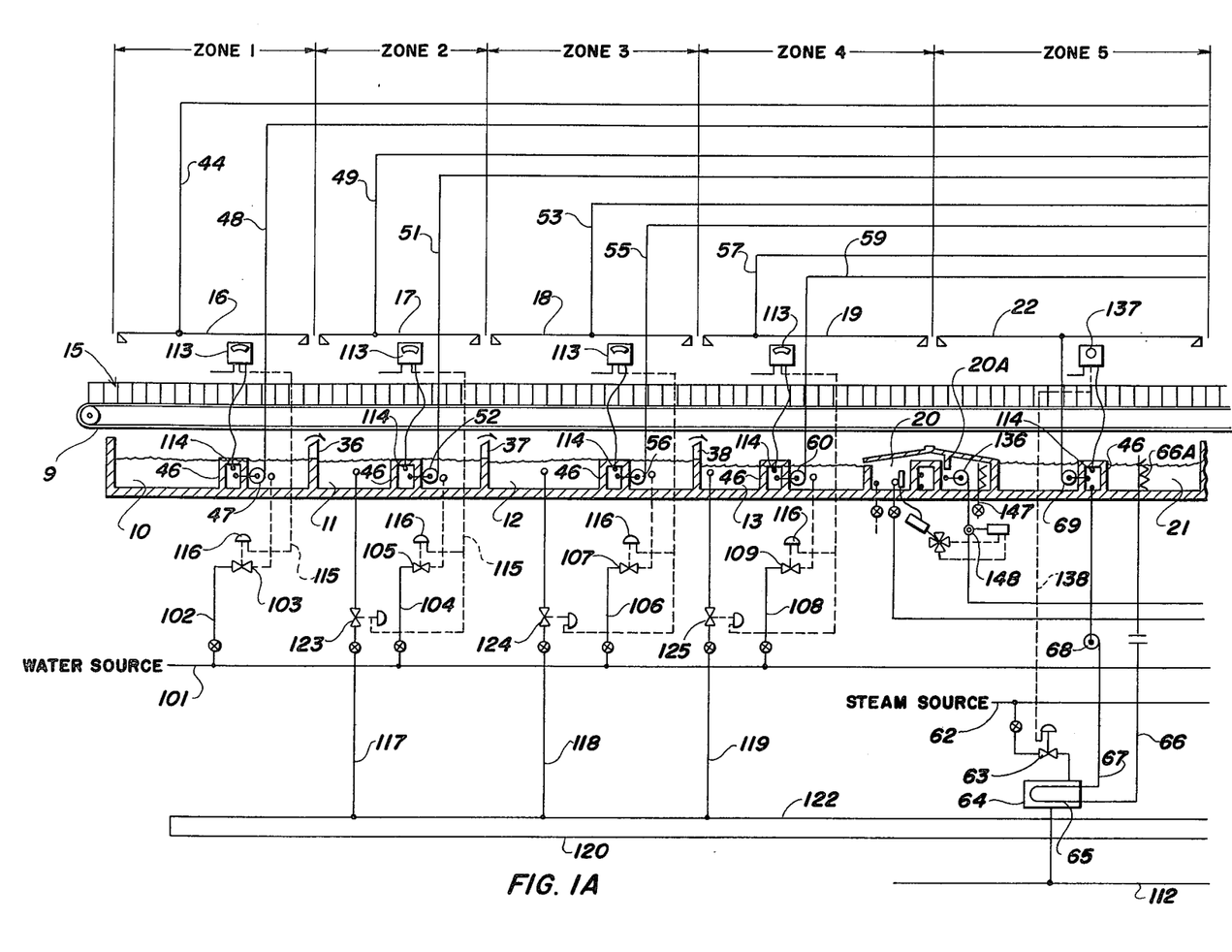
FIGS. 1A and 1B present a schematic side elevation view of a brewery pasteurizer with a diagrammatic presentation of fluid flow and controls therefor.
Figure 1B:
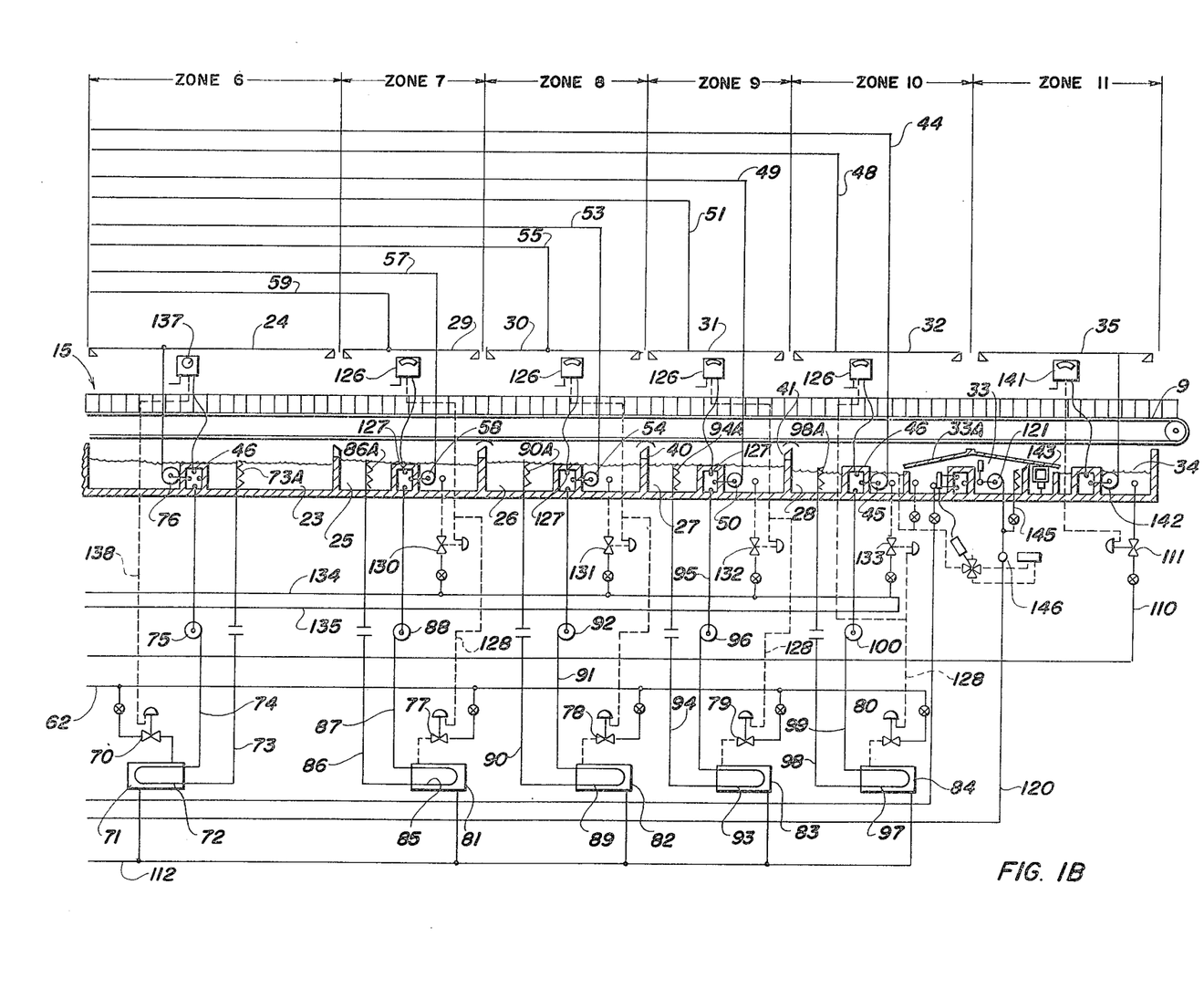

It is evident from FIGS. 1A and 1B that the cold incoming containers 15 (at a temperature of the order of 34° F.) are subject to water showered from means 16 supplied through a conduit 44 connected to pump 45 in tank 28. The pump 45 has a screen intake box 46. Each pump to be referred to is provided with an intake screen boxlike box 46 so that trash, broken glass and the like is excluded. The water collected in tank 10 is returned by pump 47 and conduit 48 to showering means 32 at tank 28. Thus, the cooled water in tank 10 after raising the temperature of the containers 15 is used at showering means 22 to cool down the containers passing tank 28. In a similar way, the showering means 17 over tank 11 is supplied by conduit 49 from pump 50 in tank 27, and showering means 31 over tank 27 is supplied by conduit 57 from pump 52 in tank 11. Likewise, showering means 18 over tank 12 is supplied by conduit 53 from pump 54 in tank 26, while showering means 30 over tank 26 is supplied by conduit 55 from pump 56 in tank 12. In like manner, showering means 19 over tank 13 and tank 20 is supplied by conduit 57 from pump 58 in tank 25, and showering means 29 over tank 25 is supplied by conduit 59 from pump 60 in tank 13. In this manner the progressive warm-up or pre-heating of the containers 15 in the first, second, third and fourth zones defined by tanks 10, 11 12 and 13 is associated with the progressive cool-down or pre-cooling of the containers 15 in zones associated with the tanks 28, 27, 26, and 25. The order of zones is reversed as the colder water in tank 10 is used to reduce the temperature of containers passing under showering means 32 to avoid thermal shock, and this progressive relationship is evident for the other pre-heating and pre-cooling zones.

The mid-zones of the pasteurizer are defined by the pasteurizing showering means 22 over special tank 20 and tank 21, and by the holding temperature from showering means 24 over tank 23. The pasteurizing temperature is obtained by the supply of steam from source 62 through controlled valve 63 and heat exchange box 64 where a coil 65 is connected into a delivery conduit 66, and a return conduit 67 has a pump 68, conduit is connected to a perforated pipe 66A so the water can circulate. The steam heats the water in tank 21 which is moved by pump 69 to showering means 22. The steam source 62 is connected through a controlled valve 70 to a heat exchange box 71 where a coil 72 is connected into conduit 73 and a return conduit 74 has a pump 75. The heated water in tank 23 is moved by pump 76 to the showering means 24. Coil 73A is perforated, like coil 66A.

The source 62 of outside steam is also connected, for use as necessary, through valves 77, 78, 79 and 80 to heat exhange boxes 81, 82, 83 and 84, respectively. Box 81 has a coil 85 connected by conduit 86 to a coil 86A in tank 25, and the return conduit 87 has a pump 88. Thus, heat imparted to water in tank 25, either from the hot containers 15 or from coil 85, is moved by pump 58 to showering means 19 to elevate temperature of the incoming containers to close to pasteurizing temperature. Box 82 has a coil 89 connected by conduit 90 to a coil 90A in tank 26 and the return conduit 91 has a pump 92. Box 83 has a coil 93 connected by conduit 94 to coil 94A in tank 27, and the return conduit 95 has a pump 96. The last box 84 has coil 97 connected by conduit 98 to coil 98A in tank 28, and return conduit 99 has a pump 100.

The source 101 of outside water (FIG. 1A) is connected by conduit 102 through control valve 103 to tank 10, and by conduit 104 through valve 105 to tank 11, and by conduit 106 through valve 107 to tank 12, and by conduit 108 through valve 109 to tank 13, and finally by conduit 110 through valve 111 to the final cooling tank 34 at the discharge end of the conveyor 9.

At the time of start up of the pasteurizer, the tanks are filled with water, except the special tanks 20 and 33 and these tanks would be almost empty when the thermal balance is reached and no gaps or skippers are encountered (as in FIGS. 1A and 1B).

The only outside water needed, after the tanks have been filled, is when the pasteurizer is provided with the last cooling zone at tank 34. This last cooling zone is provided when the containers are to be cooled down below the usual end temperature of about 80° F. Under certain conditions the water from the last cooling zone can also be stored in tank 33 and be used primarily during runout (emptying) of the pasteurizer when stored water is not normally available. This would save a substantial amount of outside water for the runout phase. Of course, steam is supplied to the boxes 64 and 71 to maintain the pasteurizing and holding temperature levels, and the condensate in boxes 64 and 71 is returned by conduit 112 to the steam generating source.

Controls for the pasteurizer water at the load end briefly comprises direct acting air pressure thermostats 113 having sensors 114 in the screen suction boxes 46 and a control connection 115 with the valve operating motors. Each load end preheat zone of the pasteurizer has a similar control arrangement. In addition, the preheat zones 2, 3 and 4 have water connections 117, 118 and 119 with a water circulating system 120 associated with the special tank 33 where a pump 121 in that tank will deliver water into the pipe 120 and, if not used, the water will be returned in pipe 122 to the tank 33. The water connections 117, 118 and 119 are controlled by valves 123, 124 and 125 respectively which are subject to the thermostats 113. If thermostats call for water, any one or more of the valves 123, 124 and 125 will open. If the water supplied from tank 33 is not sufficient, the thermostats will call for more water and one or more of the valves 105, 107 and 109 will be opened to admit outside water.

The controls for the pasteurizer pre-cool zones comprise thermostats 126 having sensor elements 127 in the screen boxes 46 and control leads 128 to the respective motor means for the valves 77, 78, 79 and 80. In addition, the thermostats 126 control hot water valves 130, 131, 132 and 133 in branch conduits connected to the hot water circulating system of conduits 134 and 135 connected to the pump 136 in the special tank 20. The pasteurizing zone and the holding zone each have a thermostat 137 with its sensor in the screen boxes 46 and a control connection 138 with the motor means for steam inlet valves 63 and 70.

WATER AND STEAM FLOW CONVENTION

Since FIGS. 1A and 1B are substantially duplicated in FIGS. 2A, 2B, 3A and 3B, it is necessary to distinguish the disclosures in the following manner; that is, by using a convention for showing when water and steam and hot water is flowing and not flowing through control valves. The convention used in these drawings is as follows: When outside water from source 101 is admitted through any of valves 103, 105, 107, 109 and 111, the conduit from each valve into the associated tank will be shown as a solid line. When any of that set of valves is closed, the conduit between it and the associated tank will be a broken line. When outside steam from source 62 is admitted to any of the heat exchangers 64, 71, 81, 82, 83 and 84, the conduit connecting the heat exchangers with the associated valves 63, 70, 77, 78, 79 and 80 will be shown as a solid line, and when any of the valves 63, 70, 77, 78, 79 and 80 is closed, the conduit will be shown as a broken line.

As start up of the pasteurizer, that is when cool containers start into the load end on conveyor 9, the tank 20 is not filled with water, but the heat exchange boxes 64, 71, 81, 82, 83 and 84 need to be receiving steam from source 62. Also, all circulating pumps 47, 52, 56, 60, 69, 76, 58, 54, 50 and 45 are operating to initiate water sprays throughout the length of the pasteurizer. There is, at start up, no flow of hot containers through the pre-cool zones associated with tanks 25, 26, 27 and 28.

The absence of hot containers, therefore, requires the introduction of heat from the steam source 62 through the heat exchange boxes 81, 82, 83 and 84 so that the water in the associated tanks 25, 26, 27 and 28 can be elevated in temperature and that heated water transmitted by the associated pumps to the load end of the pasteurizer for delivering the heated water through the sprays for purposes of raising the temperature of the incoming containers to a level suitable for movement through the pasteurizing and holding zones which are provided with heated water through showering means 22 and 24. The heated water in these two zones is obtained by steam heat exchange in boxes 64 and 71 so that the heated water circulated by pumps 68 and 75 will maintain the water temperature in tanks 21 and 23 at the proper level of temperature in a circulating circuit in conduits 66, 67 and 73, 74. The pumps 69 and 76 in those respective tanks can supply the showering means 22 and 24 in separate circulating circuits. As a full complement of containers is obtained in the pasteurizer, the system of heat exchange reaches a thermal balance as shown in FIGS. 1A and 1B.

IDEAL OPERATION

The ideal operation of the pasteurizer is reached when there is an uninterrupted supply of containers and all zones are loaded with containers. Such a condition is illustrated in FIGS. 1A and 1B. Using the above convention, it is seen that outside water is flowing only through valve 111 to tank 34 for circulation by pump 142 to sprays 140 and all other valves 103, 105, 107 and 109 are closed. Cool water from tank 33 is moved by pump 121 and conduit 120 to and through valves 123, 124 and 125 so it can be delivered by pumps 52, 56 and 60 to the pre-cooling showering means 31, 30 and 29. The source of steam 62 is connected to heat exchangers 64 and 71 to heat the circulating water in conduits 65 and 72 for the pasteurizing zone 5 and holding zone 6. No steam is admitted through valves 77, 78, 79 and 80 to the heat exchangers 81, 82, 83 and 84. The hot water storage tank 20 is only partially filled with water, and in the ideal condition, no heated water is being admitted through valves 130, 131, 132 and 133.

A more realistic operating condition is usually encountered in that the supply of containers would be fairly consistent at about 85% of the capacity of the conveyor. This means that there will be gaps or skippers marked by the absence of containers on the conveyor in the pre-heat zones and eventually in the pre-cool zones. These zones are especially important since it is critical to the efficiency of the pasteurizer when handling glass containers to avoid glass breakage because of thermal shocks.

WATER CONSERVATION PHASE

Figure 2A:
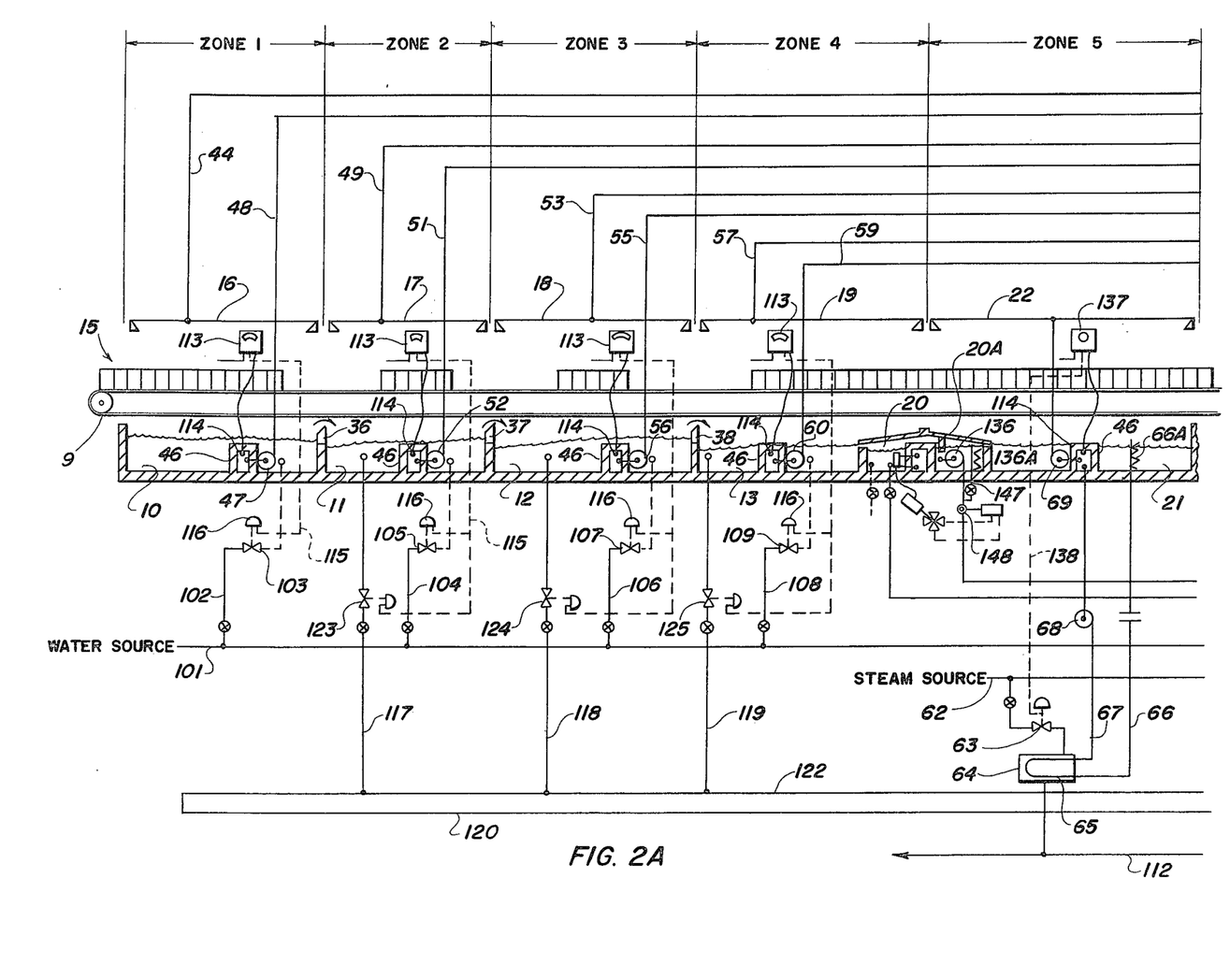
FIGS. 2A and 2B present a schematic side elevation view similar to FIGS. 1A and 1B, but showing the active water conservation system.
Figure 2B:
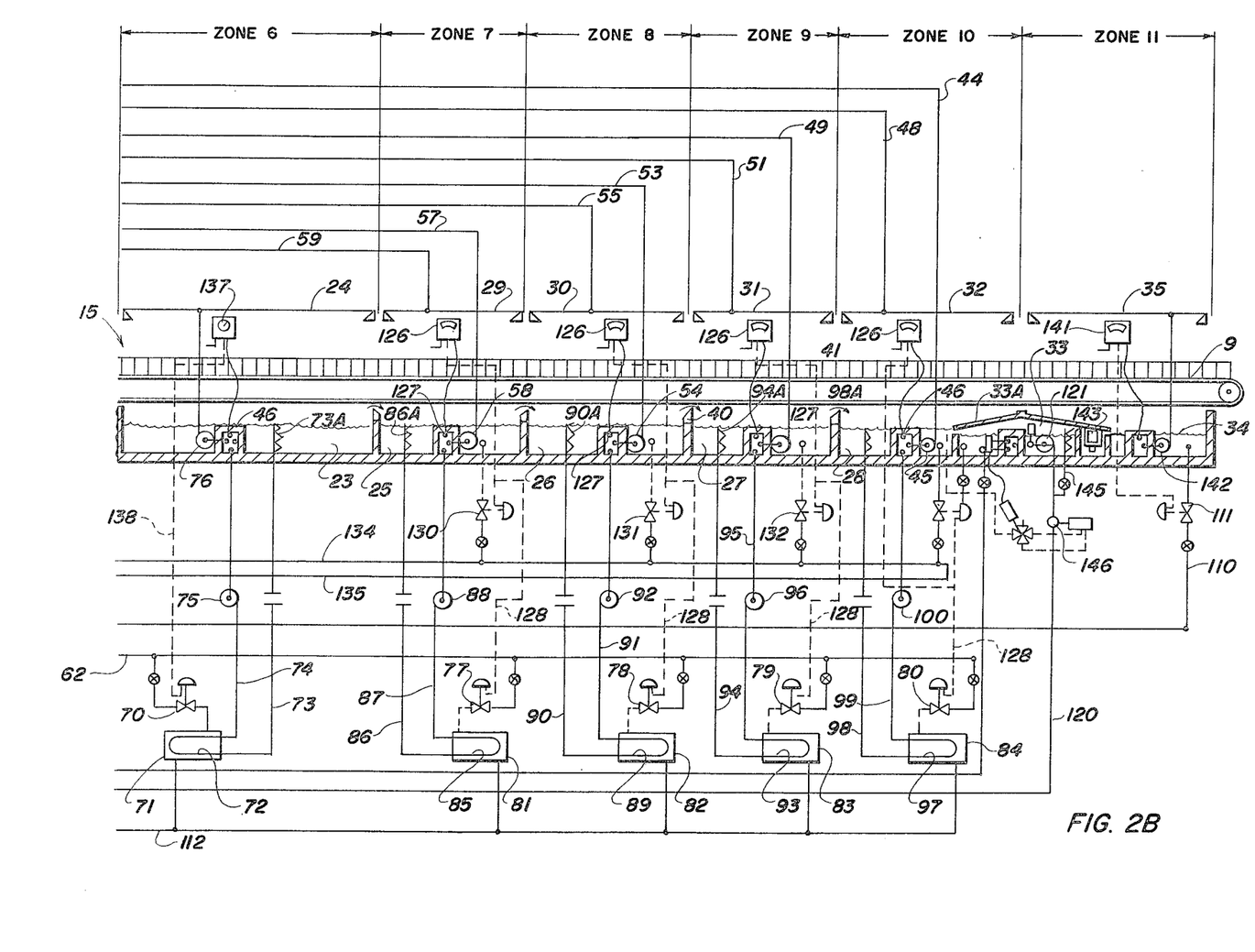
Figure 3A:
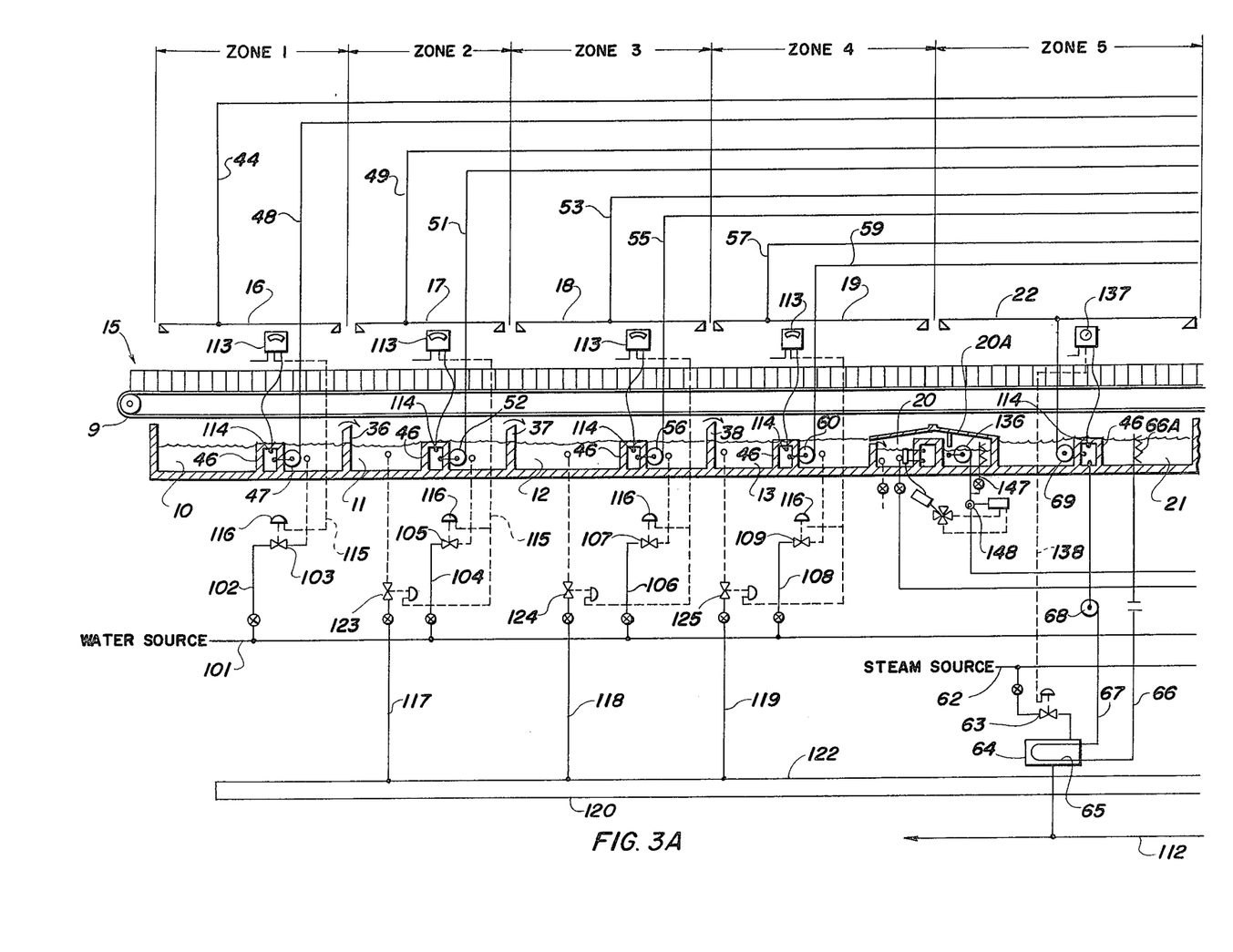
FIGS. 3A and 3B present a schematic side elevation view similar to FIGS. 1A and 1B, but showing the active steam conservation system.
Figure 3B:
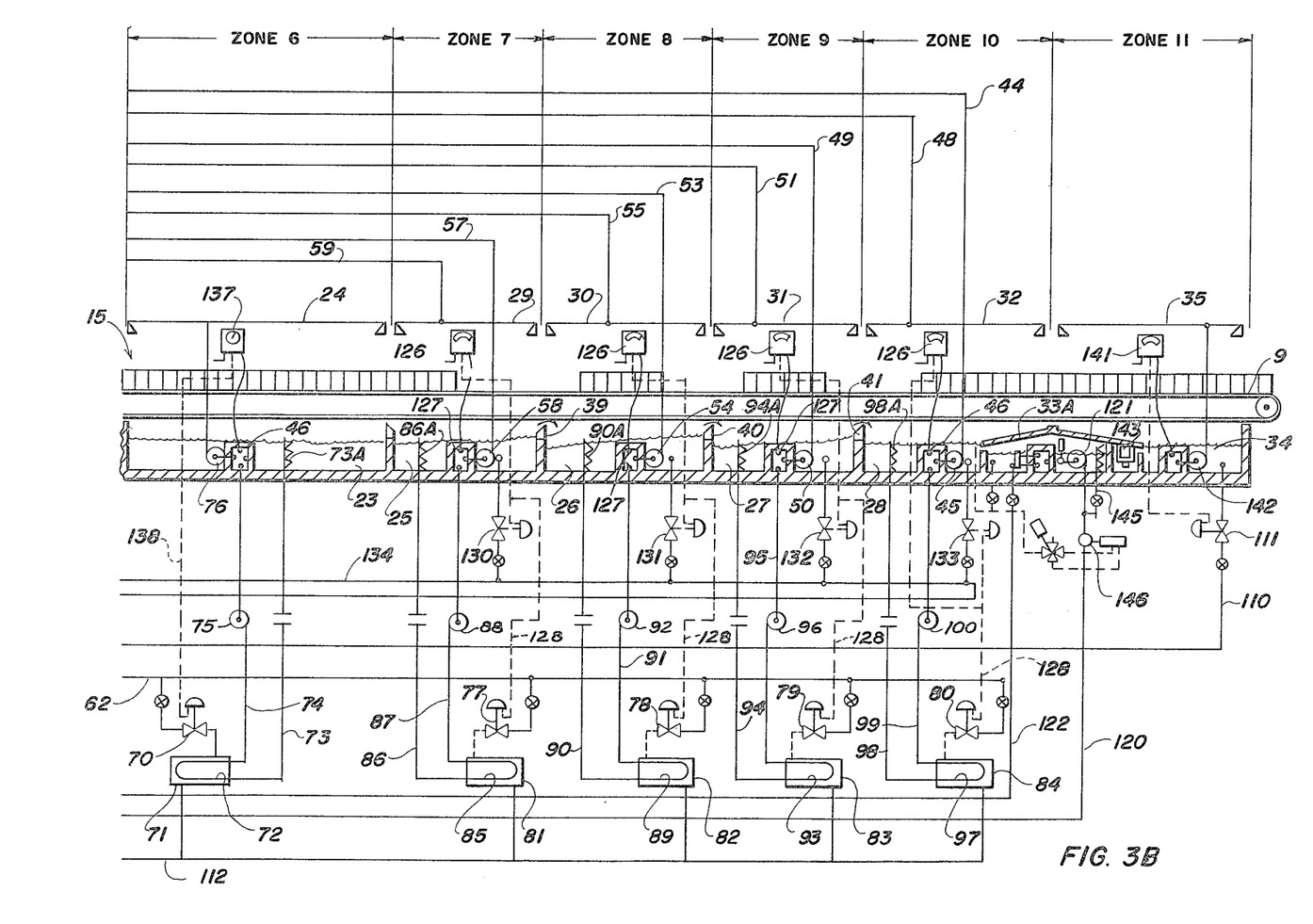

In FIGS. 2A and 2B, the water in tank 10 and the showering means 16 in zone one over tank 10 are in normal water exchange relation with the showering means 32 in zone ten and water in tank 28. Thus, the cold containers over tank 10 extract heat from the water delivered by showering means 16, thereby picking up heat, and the cooled water in tank 28 is heated by the hot containers passing under showering means 32. Pumps 47 and 45 operate to move the water between these two zones one and ten. The same normal relationship is established between showering means 17 in zone two over tank 11 and showering means 31 in zone nine over tank 27. Thus, they are in exchange relationship by virtue of the operation of pumps 52 and 50. Similarly, showering means 18 in zone three over tank 12 and showering means 30 in zone eight over tank 26 are in exchange relationship by virtue of the operation of pumps 56 and 54. Finally, showering means 19 in zone four over tank 13 and showering means 29 in zone seven over tank 25 are in exchange relationship by virtue of the operation of pumps 60 and 58. In this manner the cooling effect of the incoming containers is imparted to the heated outgoing containers and the heat extracted from the heated containers to pre-cool them is given up to pre-heat the cold containers.

However, when skippers appear in the incoming flow of containers, there is an unbalance in the apparatus, so the thermostats 113 call for cool water in the tanks 10, 11, 12 and 13 to take the place of the lack of cold containers. The cool water comes from the outside water source 101 and from the cool water collected in tank 33 upon opening of valve 146 and delivered from pump 121 in conduit 120 and through now open valves 123, 124 and 125. The water admitted from source 101 is now excess water and spills through weirs 36, 37 and 38 into the respective tanks 11, 12 and 13. This water is warmed up by the showering means 17, 18 and 19 due to the skippers in these zones two, three and four. The water is increasingly raised in temperature due to the fact that the hottest containers from the pasteurizing and holding zones five and six raise the water temperature in tanks 25 and 26 the most. The heated water in tank 13 is collected in tank 20 and is recirculated by pump 136 through the perforated coil 136A as long as valve 148 is closed. It is evident that a substantial quantity of the water already in the various tanks is being used to handle the presence of skippers, and that reduces the amount of outside water from source 101 to about fifty percent of the total water required.

STEAM CONSERVATION PHASE

As the skippers pass through the pasteurizing zones five and six and enter the pre-cooling zones (FIGS. 3A and 3B), a different sequence of events takes place. The lack of hot containers in zones seven, eight, nine and ten allows the water from showering means 29, 30, 31 and 32 to fall into tanks 25, 26, 27 and 28 without gaining heat which is expected to be moved by pumps 58, 54, 50 and 45 into the pre-heating zones one, two, three and four. Thermostats 113 close the water valves 103, 105, 107, 109 and valves 123, 124 and 125. However, thermostats 126 call for hot water and open valves 130, 131, 132 and 133 to obtain stored heated water from tank 20 which is then pumped into the pre-heating zones as a substitute for the lack of heated containers. The water from tank 20 is admitted to the pre-cooling tanks upon opening of valves as noted above, without the need for steam as valves 77, 78, 79 and 80 remain closed. That heated water causes the tanks 25, 26, 27 and 28 to fill up to the level where they overflow through weirs 39, 40 and 41 and finally the water is collected in tank 33. In the flow of water toward tank 33, it will become cooler on the basis of the showering means 31 and 32 being supplied with water from the coolest zones at the load end.

FINAL COOLING PHASE

It is sometimes required that the discharged containers should be cooled to a temperature in the range of about 70° F., rather than at a temperature somewhat higher, as in the range of about 80° F. This final cool-down is provided by incorporating the showering means 35 over the tank 34. The water for tank 34 is supplied by conduit 110 when the thermostat 141 opens valve 111, the thermostat being set for the lower temperature to supply water which is pumped by pump 142 to the showering means 35. The system is arranged so that the water in tank 34 can flow into the water conservation tank 33, and excess water at a desirably low temperature is allowed to run off to sewer at the overflow outlet 143. If the final cooling stage is required, there is the added advantage of always having water available in tank 43 which can be used not only for a skipper, but also when a complete runout is occurring, thus saving a considerable amount of water.

RESUME

It should be understood from the foregoing description that during the presence of gaps or skippers in the load end of the pasteurizer there are no cool containers to be showered with water heated by the containers moved through the pre-cooling zones after pasteurizing. Therefore, the water in the tanks at the load end gets heated up. This condition is corrected by responses of the thermostats 113 which call for cool water by opening valves 103, 123, 124 and 125. The opening of valve 103 admits outside water which is pumped over to showering means 32 for cooling the containers, and is returned at higher temperature to showering means 16 over tank 10 by pump 45. The opening of valves 123, 124 and 125 admits water moved by pump 121 from the water conservation tank 33 into tanks 11, 12 and 13. However, the excess water in tanks 10, 11, 12 and 13 flows through the respective weirs 36, 37 and 38, and is collected in the tank 20. Now, when the gaps or skippers appear in the movement of containers through the pre-cooling end of the pasteurizer, a reverse operation takes place. The water in tank 13 moved by pump 60 is released at showering means 29 and overfills tank 25. The excess water passes out of tank 25 and into tank 26 through weir 39. This overflow continues through weirs 40 and 41. Concurrently, the lack of hot containers passing under showering means 29, 30, 31 and 32 deprives the load end showering means 16, 17, 18 and 19 of hot water to pre-heat the flow of incoming containers. Thermostats 113 close valves 102, 123, 124, and 125, while thermostats 126 call for heated water and open valves 130, 131, 132 and 133 to draw water from the hot water tank 20 by action of pump 136 through pipe 134. The use of the hot water from tank 20 conserves the use of steam.

Since the pumps throughout the pasteurizer are energized during operation, it is necessary to provide a recirculating or by-pass circuit for pump 121. The by-pass is formed by conduit 145 in conduit 120 and becomes effective when the motorized valve 146 is operated to shut-off conduit 120. Also pump 136 in tank 20 is provided with a similar by-pass conduit 147 controlled by motorized valve 148 in conduit 134. Other controls include those for valves 105, 107 and 109 which respond to open conduits 104, 106 and 108 should the water conserved in tank 33 be insufficient to handle the passage of gaps or skippers in the movement of containers. In like manner, if the hot water conserved in tank 20 is insufficient to handle the gaps or skippers in the discharge zones, valves 77, 78, 79 and 80 will be opened to admit steam from source 62. However, the means for conserving on the use of outside water and for reducing the use of steam to only the pasteurizing and holding zones is sufficient to handle normal container skipper situations within allowable tolerances.

What is claimed is:

1. A process of conserving the use of water and steam in pasteurizing the contents of containers which comprises: moving the containers from a load end through successive pre-heating showering zones for delivering a heating liquid onto said containers to progressively elevate the contents of the containers toward pasteurizing temperature, then through pasteurizing and temperature holding showering zones for delivering a liquid onto said containers at a pasteurizing temperature, and thence through successive pre-cooling showering zones for delivering a cooling liquid onto said containers to a discharge end; interchanging water between the successive pre-heating zones and successive pre-cooling zones and showering the containers in such zones for maintaining substantial thermal balance in the process; supplying steam for elevating the temperature of water to effect pasteurization of the contents of the containers; storing heated water collected from the pre-heating and pasteurizing zones; collecting cooling water from the pre-cooling zones; and on the occurrence of skippers entering the loading end, applying the stored heated water and the collected cooling water to the respective pre-cooling and pre-heating zones in a predetermined sequence for substantially sustaining the thermal balance between the pre-heating and pre-cooling zones as the skipper progresses to the discharge end.

2. A method for conserving the use of outside water and the use of steam during movement of skippers through container pasteurizing apparatus having a series of pre-heating showering zones leading into and a series of pre-cooling showering zones leading from a pasteurizing showering zone, the method comprising:
   (a) collecting heating water showered into the pre-heating zones from the pre-cooling zones and holding the collected heating water adjacent the pasteurizing zone;
   (b) collecting cooling water from the pre-cooling zones and holding the collected cooling water for movement into the series of pre-heating zones for showering in the series of pre-cooling zones;
   (c) sensing the increased temperature of water in the series of pre-heating zones due to the presence of skippers, and admitting cool ambient water and cooling water collected from the series of pre-cooling zones into the series of pre-heating zones for movement into the series of pre-cooling zones to substitute for the missing cooling effect caused by the skipper in the pre-heating zones; and
   (d) sensing the decreased temperature of water in the series of pre-cooling zones due to the presence of skippers moved into the pre-cooling zones, and admitting said heating water from the collected heating water into the series of pre-cooling zones for movement into the series of pre-heating zones to substitute for the missing heating effect caused by the skipper in the pre-cooling zones.

3. The method of claim 2, wherein the series of pre-heating zones are in water flow exchange relation with the series of pre-cooling zones in an inverse order such that the containers leading into the apparatus move through a first one of the pre-heating zones and the containers leading from the apparatus move through a remote one of the pre-cooling zones.

4. The method of claim 2, wherein the collected heating water is held in a recirculating flow adjacent the pasteurizing zone for retaining heat approaching that of the pasteurizing zone.

5. The method of claim 2, wherein the collected cooling water is held in a recirculating flow adjacent one of the series of pre-cooling zones, and a final cooling zone is in supply connection with the held cooling water for feeding ambient water thereto and for runoff to sewer.

* * * * *